United States Patent
Broz et al.

(10) Patent No.: US 6,752,012 B2
(45) Date of Patent: Jun. 22, 2004

(54) COMBINED ELECTRICAL TEST AND MECHANICAL TEST SYSTEM FOR THIN FILM CHARACTERIZATION

(75) Inventors: Jerry J. Broz, Longmont, CO (US); Cheryl D. Hartfield, McKinney, TX (US); Reynaldo M. Rincon, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 10/061,740

(22) Filed: Jan. 31, 2002

(65) Prior Publication Data

US 2003/0140684 A1 Jul. 31, 2003

(51) Int. Cl.$^7$ .................................................. G01N 17/00
(52) U.S. Cl. ................................... 73/150 R; 73/866.4
(58) Field of Search ........................... 73/81, 82, 150 R, 73/150 A, 866.4, 866; 324/691 R, 693, 713, 719, 722, 765, 761

(56) References Cited

U.S. PATENT DOCUMENTS 5,309,754 A  *  5/1994  Ernst ............................. 73/81

OTHER PUBLICATIONS

Randall, et al., "Characterization of integrated circuit aluminium bonding pads by nonoindentation and scanning force microscopy," *Surface and Coatings Technology*, vol. 99, pp. 111–117, 1998.

* cited by examiner

Primary Examiner—Robert Raevis
(74) Attorney, Agent, or Firm—Frederick J. Telecky, Jr.; W. James Brady, III

(57) ABSTRACT

An apparatus (30) and method (80) for predicting electrical property stability of a thin film or conductive substrate (14) prior to multi-probe testing. The present invention utilizes a nanoindenter type device (10) obtaining mechanical properties as a function of displacement depth and applied load into the bond pad surface to accurately predict electrical property stability of the entire substrate or sample under test. In addition, the present invention includes a nanoindenter type device (10) including a second probe (34) having the ability to measure localized electrical properties of the sample while obtaining the mechanical property measurements. This additional electrical measurement is correlated with the mechanical property measurements to accurately predict electrical property stability of the entire conductive substrate, preferably by predicting the presence of an unwanted material surface layer.

9 Claims, 4 Drawing Sheets

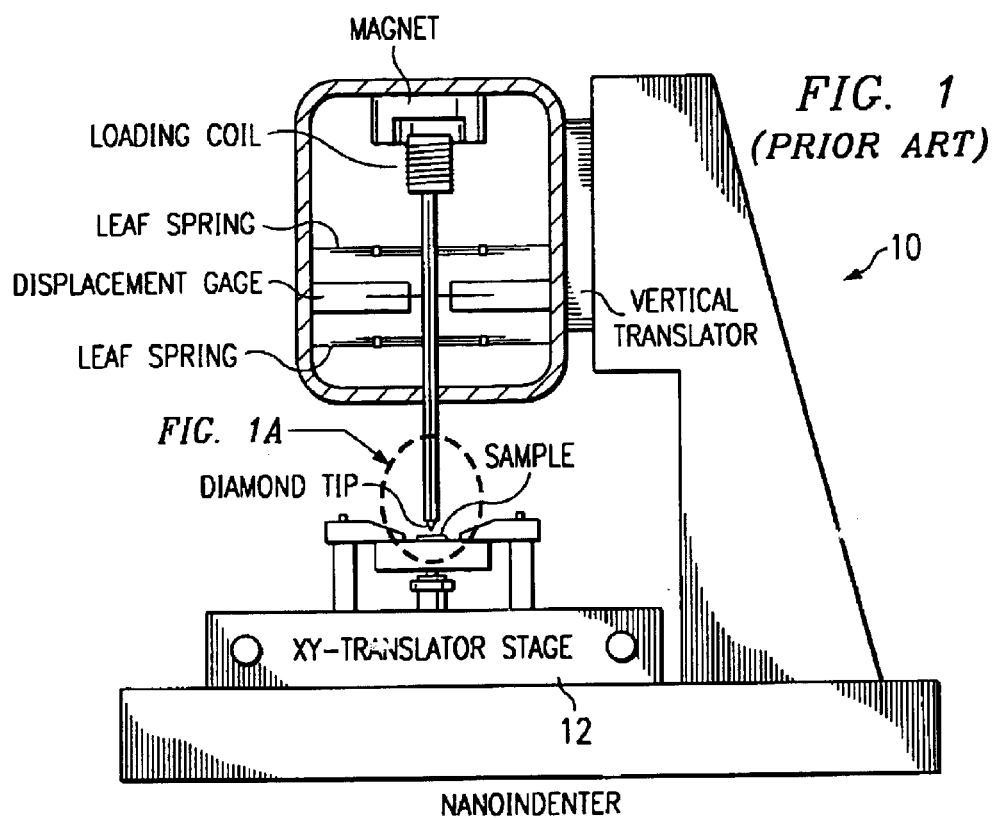
FIG. 1 (PRIOR ART)
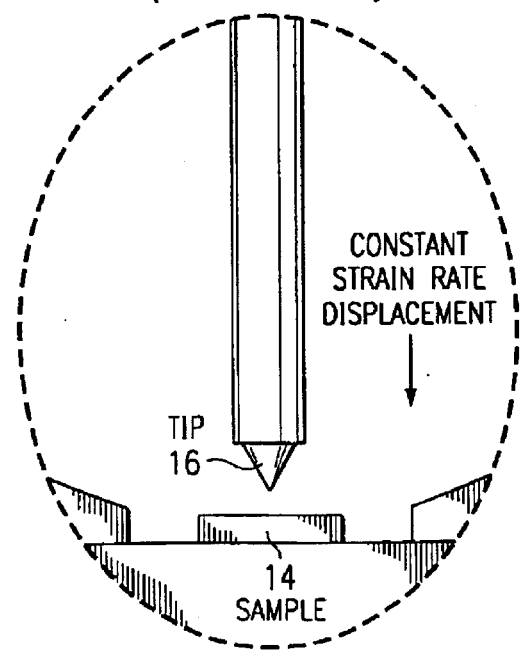
FIG. 1A (PRIOR ART)
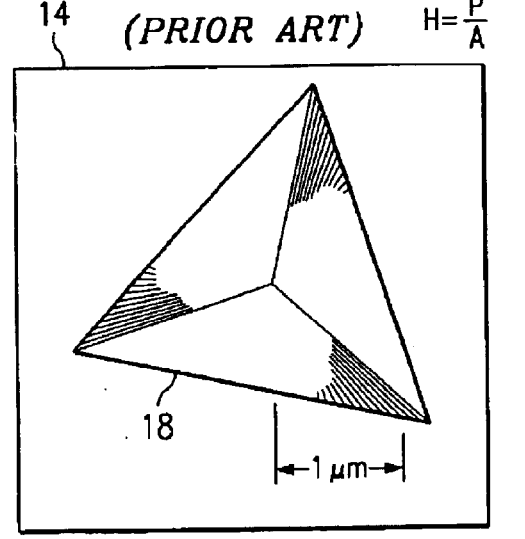
FIG. 2 (PRIOR ART)   $H = \dfrac{P}{A}$

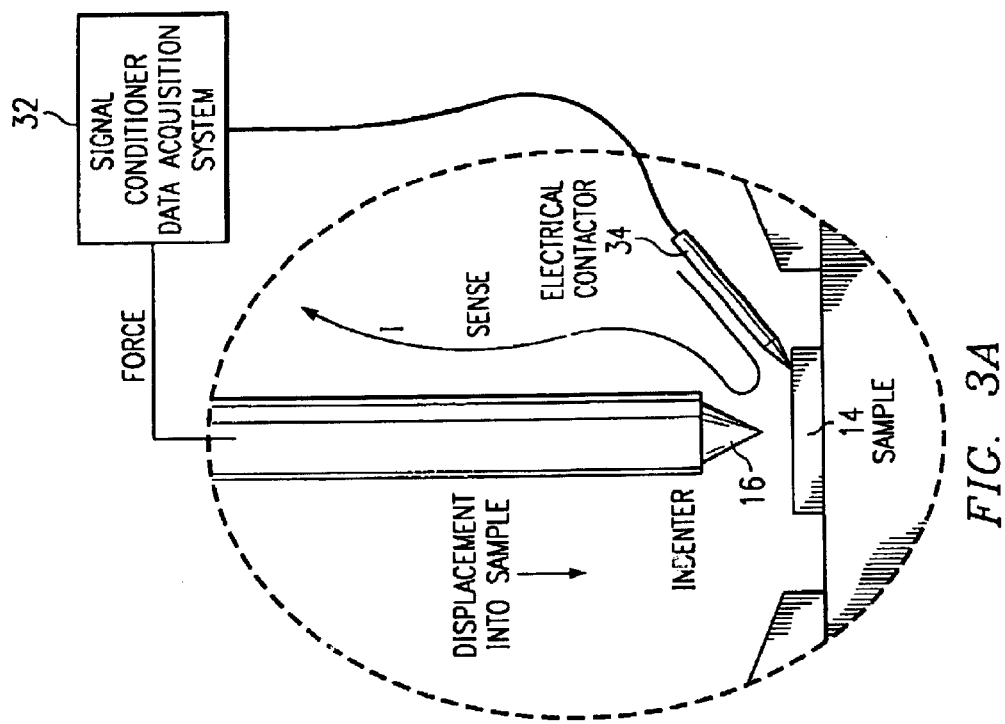
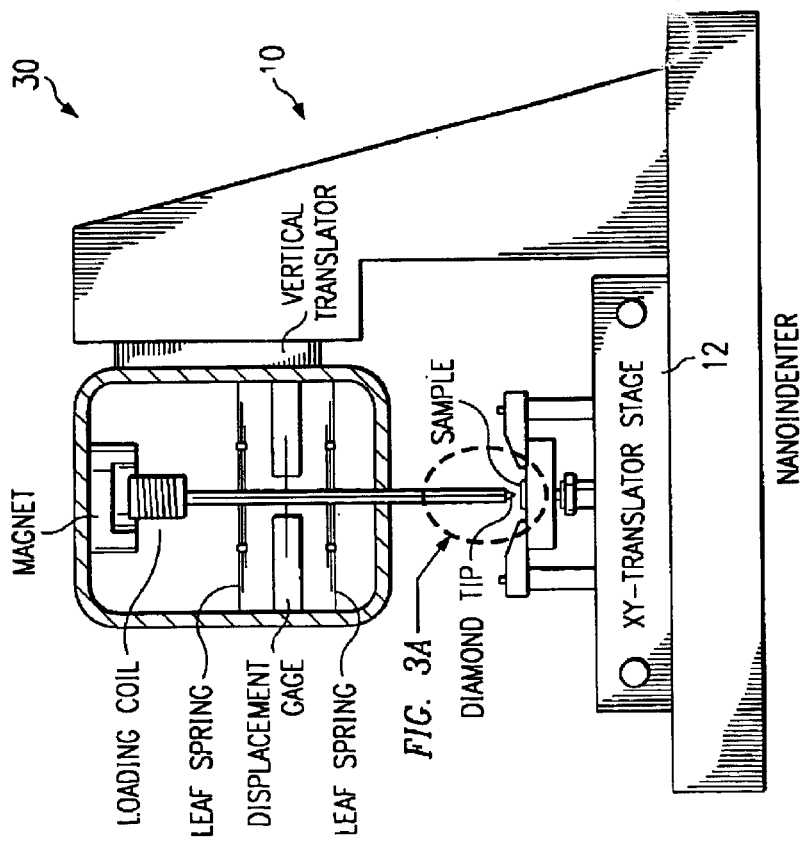

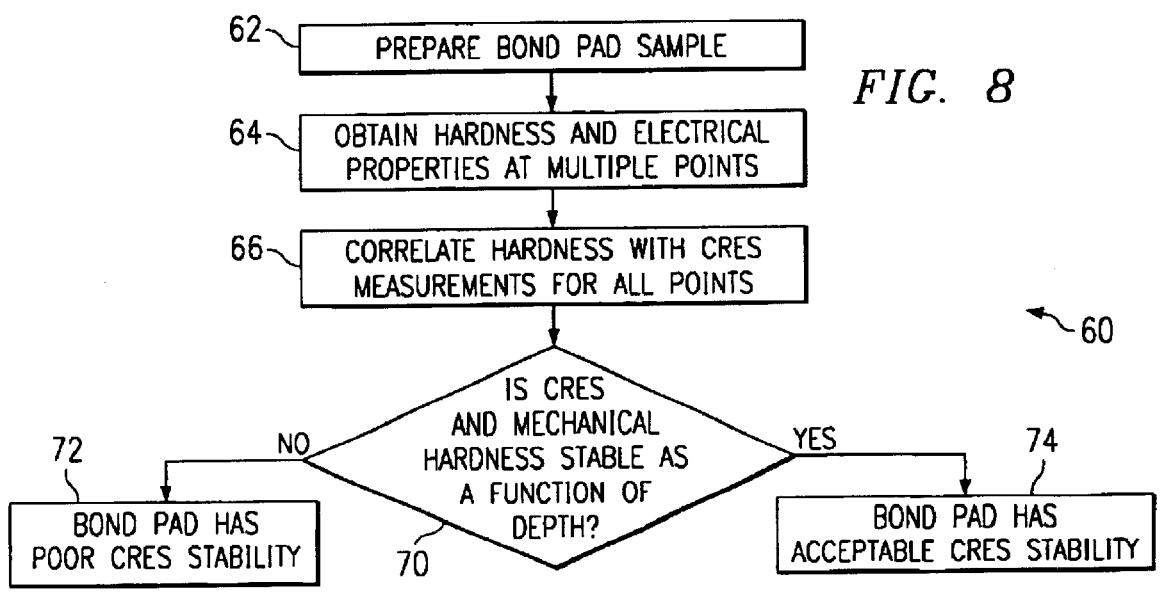

FIG. 6 — CONTACT RESISTANCE vs DIE TOUCHDOWNS (58)

FIG. 7 — CONTACT RESISTANCE vs DIE TOUCHDOWNS

FIG. 8

- 62 — PREPARE BOND PAD SAMPLE
- 64 — OBTAIN HARDNESS AND ELECTRICAL PROPERTIES AT MULTIPLE POINTS
- 66 — CORRELATE HARDNESS WITH CRES MEASUREMENTS FOR ALL POINTS
- 70 — IS CRES AND MECHANICAL HARDNESS STABLE AS A FUNCTION OF DEPTH?
  - NO → 72 — BOND PAD HAS POOR CRES STABILITY
  - YES → 74 — BOND PAD HAS ACCEPTABLE CRES STABILITY
- 60

COMBINED ELECTRICAL TEST AND MECHANICAL TEST SYSTEM FOR THIN FILM CHARACTERIZATION

FIELD OF THE INVENTION

The present invention is generally related to the field of semiconductor material testing and analysis, and more particularly to the field of surface characterization and assessing the surface properties of a semiconductor material including thin films for a semiconductor die under test.

BACKGROUND OF THE INVENTION

An integrated circuit typically includes a packaged semiconductor die including electrical circuitry formed upon a wafer substrate. Bond pads are typically employed to provide an electrical/mechanical interface between pin packaging and the signal lines defined in the die. These bond pads are a crucial portion of the overall integrated circuit package in that they need to provide a reliable electrical interface to the die for multi-point testing prior to final assembly. Hence, the reliability and testability of these bond pads are an important component of the semiconductor process.

The bond pad surface composition can be effected by wafer fab processing steps that include deposition and etch of metals, oxides, barrier and protective overcoat (PO). It is known that changes in any of the wafer fab processing steps can adversely affect the contact resistance stability of the bond pad during a multi-probe testing of a die under test (DUT). During multi-probe testing, a test current flowing between a probe needle and the bond pad, such as aluminum pad, is constricted to the intermetallic contact areas, commonly known as a-Spots, and across any thin conductive or semi-conductive films. The contact resistance (CRES) across the interface is comprised of the constriction resistance plus the interfacial film resistance. The CRES magnitude and stability are entirely attributable to the interfacial phenomena that occur between the probe contact area and the bond pad surface composition. High and unstable contact resistance during multi-probe disadvantageously results in yield fallout and false device failure identification.

Understanding of the bond pad surface composition is critical to ensure process optimization that will enable a surface with good properties for high multi-probe yield, and once optimized, implement process control monitoring at the bond surface.

Elemental surface analysis of the bond pad is a typical strategy employed for identifying types of molecules present on the bond pad surface. Industry-wide, characterization is typically performed using various surface analysis techniques that include auger electron spectrometry, time of flight secondary ion mass spectrometry (ToF-SIMS), x-ray photoelectron spectroscopy (XPS), atomic force microscopy (AFM) and Fourier transform infrared spectroscopy (FTIR). Transmission electron microscopy (TEM) and Scanning electron microscopy (SEM) are also used.

For many of these techniques, the results can be compromised by an analyst's bias regarding the region chosen for analysis, and the analysis "spot size" is to small to lend insight into the "global" surface properties. For instance, a 30 Angstrom sampling spot on one bond pad may not be representative of the entire bond pad, or of all bond pads on a die, etc. Investigative work shows as a result of the small sampling area and site-specific nature of most of these techniques that it is difficult to show a correlation between a specific compositional property and contact resistance behavior at multi-probe.

There is desired a technique suitable for process control (in-line or at-line) that can provide clear and rapid feedback at relatively low cost, and that can determine and predict whether a bond pad surface composition is suitable for accurate multi-probe testing when the associated semiconductor die is later subjected to testing, such as during product validation.

SUMMARY OF THE INVENTION

The present invention achieves technical advantages by using a nanoindenter type device to determine localized mechanical properties of a substrate (such as a bond pad) as a function of displacement depth or applied load of the nanoindenter tip into the substrate surface, and accurately predicting the electrical property stability of the substrate under test as a function of this data. In a further embodiment, the nanoindenter type instrument is modified to further include a localized electrical measurement capability whereby the measured electrical property is correlated to the mechanical property measurement and displacement depth or applied load to understand substrate or thin film surface composition and its subsequent suitability for multi-probe testing.

The present invention includes a method and apparatus that determines a substrate or thin film surface mechanical property as a function of displacement depth or applied load of the nanoindenter tip into the substrate under test. In one embodiment, it is expected that measured mechanical properties (such as material hardness) will decrease as a function of displacement depth or applied load onto the sample. Advantageously, this data is utilized to accurately predict the electrical property stability of the conductive substrate or bond pad to determine its suitability for multi-probe at a later process step. This data processing of the present invention provides for predicting the presence of an unwanted layer material on the substrate surface, such as due to a change in a wafer fab processing, which this layer will lead to subsequent multi-probe testing problems. Using nanoindentation has the advantageous features of being low cost compared to other techniques, is capable of sampling a large surface area, is less time intensive, and is significantly easier to interpret by a "non-expert". As such, nanoindentation has these many qualities that make it suitable for monitoring fab process changes that may impact electrical properties and which may adversely effect subsequent multi-probe testing of the die under test. An additional simultaneous measurement of electrical properties while obtaining mechanical properties as a function of nanoindenter tip displacement depth and applied load into the surface further provides for the prediction that the substrate electrical property stability.

BRIEF DESCRIPTION OF THE DRAWINGS

FIG. 1 is a side view of a conventional nanoindenter typically utilized to determine elastic modulus and the material hardness of a sample;

FIG. 2 depicts a top view of an indentation formed in the sample by the nanoindenter, wherein hardness is determined as a function of the pressure applied as a function of the area defined by the indentation;

FIG. 3 depicts an apparatus and method of the present invention whereby a nanoindenter is utilized to sample a bond pad and predict the contact resistance stability of the bond pad by comparing the determined material hardness as a function of displacement depth, and further, if desired, also measuring localized contact resistance simultaneously to validate the predicted contact resistance of the overall bond pad;

FIG. 6 depicts test data for the peaked curve in FIG. 5 when the measured material hardness as a function of displacement depth does not follow the predicted curve, depicting a high bond pad hardness with poor electrical behavior and inconsistent contact resistance;

FIG. 7 depicts data for the curve of FIG. 5 whereby the material hardness as a function of displacement depth follows the anticipated decreasing curve, validating for multiple points a consistent low contact resistance and low bond pad hardness, thereby predicting good contact resistance stability and the absence of an unsuitable layer formed upon the bond pad surface; and FIG. 8 is a flow diagram of the method of the present invention which predicts whether or not the bond pad had good contact resistance stability by analyzing the bond pad hardness as a function of displacement depth of the nanoindenter into the bond pad under test.

DETAILED DESCRIPTION OF THE PREFERRED EMBODIMENT

Figure 4:
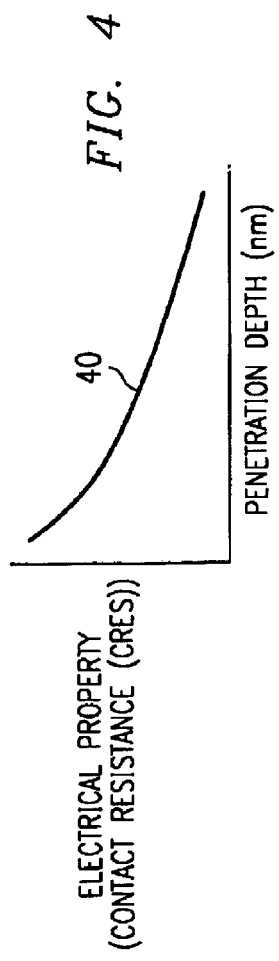
FIG. 4 plots an expected curve of the electrical contact resistance as a function of penetration depth of the nanoindenter probe into the bond pad surface.

Referring now to FIG. 1, there is generally shown at 10 a nanoindenter 10 including an X-Y translator stage 12 supporting a sample 14 under test. The nanoindenter is seen to include a diamond triangular-shaped tip probe 16 which is vertically displaced into the sample 14. The conventional nanoindenter 10 is typically used to measure mechanical properties of the sample under test, and is frequently used by applying a load and measuring a depth of displacement of the tip into the sample to determine elastic modulus and the material hardness.

FIG. 2 depicts a triangular indentation 18 that may be formed into the sample 14 by the triangular shaped tip 16. Typically, hardness is measured by the following equation;

$$H=P/A$$

Whereby P=pressure and A=the area of the indentation 18.

Referring now to FIG. 3, there is depicted a preferred embodiment of the present invention at 10 whereby the nanoindenter 10 is further provided with a signal conditioner data acquisition system 32 which processes the data provided by the nanoindenter, and advantageously correlating the mechanical and/or electrical properties of the bond pad under test 14 to accurately predict the contact resistance stability of the bond pad. The apparatus 30 is seen to be further provided with an electrical probe 34 which makes electrical contact with the sample under test proximate the indentation and which completes an electrical circuit between the nanoindenter probe tip 16 via the sample. Accordingly, localized contact resistance between the tip 16 and electrical probe 34 can be ascertained at the sample location proximate where the indenter is displaced into the sample under test.

The signal conditioner data acquisition system 32 preferably includes a processor, such as a digital signal processor or other suitable hardware and software, to both obtain and process the data generated by apparatus 30 as will now be discussed.

Turning to FIG. 4, there is depicted the predicted electrical contact resistance of a sample under test as a function of penetration depth of the probe tip into the sample under test. A nominal characteristic curve 40 is obtained for materials used in bond pads determined to be within process limits established for a particular semiconductor process. The apparatus 30 of the present invention can both ascertain the localized contact resistance as a function of penetration depth, and can process the data to determine if it is within tolerance of the expected measurements.

Figure 5:
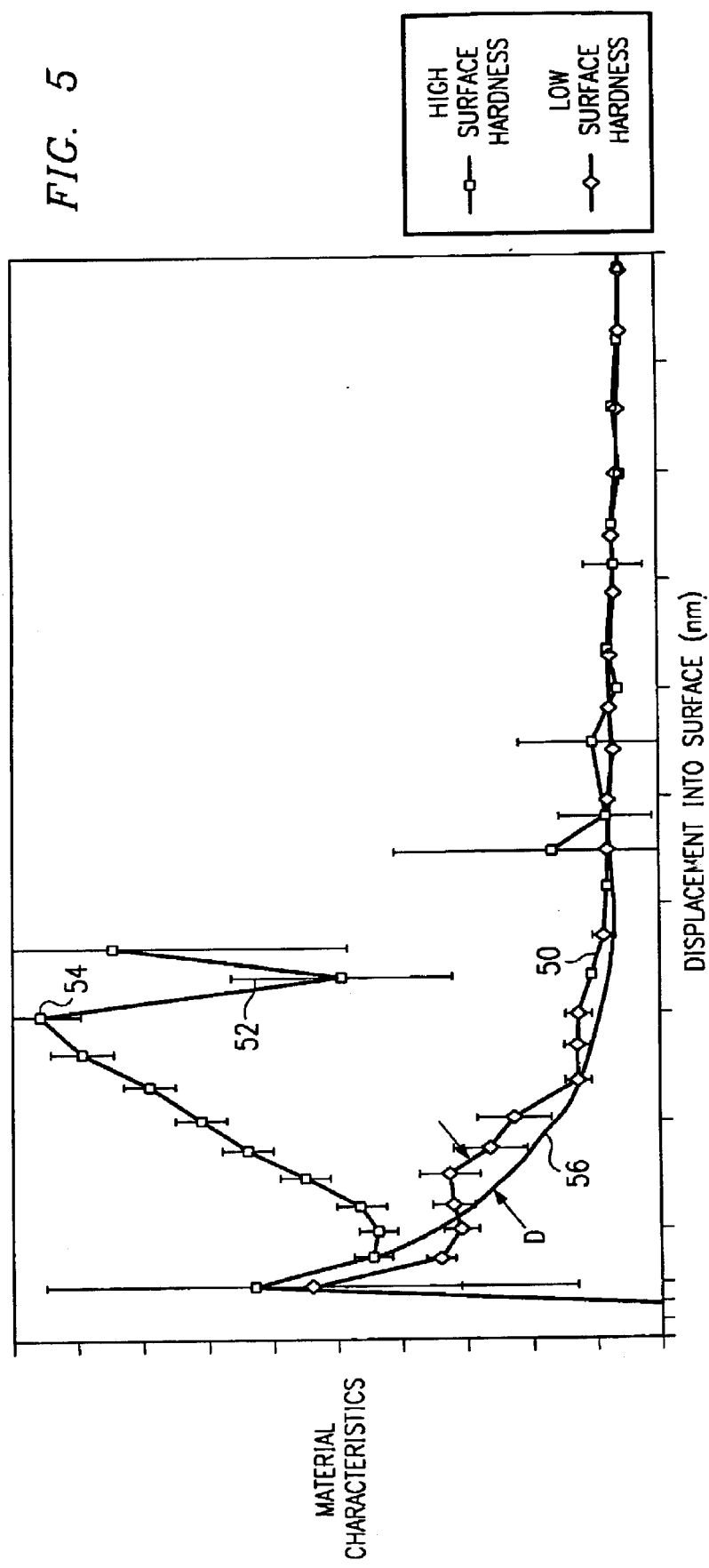
FIG. 5 depicts a graph of data depicting in one instance a bond pad having good contact resistance stability, and depicting data in another instance when the bond pad is predicted to have a unsuitable contact resistance stability.

Turning now to FIG. 5, there is depicted a curve 50 and 52, which curves are a plot of the material hardness of the bond pad as a function of displacement depth of the nanoindenter tip 16 into the bond pad under test. The lower descending curve 50 is plots test data depicting the material hardness measurement seen to slowly decrease as a function of displacement depth of the nanoindenter into the bond pad under test. This plot conforms with an expected plot 56, whereby the data points may, for instance, all be within 20% of an nominal expected curve 56. Of course, other parameters and process guidelines can be utilized to determine whether or not the obtained data is determined to fall within, or not fall within, process guidelines. For a sample under test that has good electrical behavior, i.e., has a good contact resistance stability, curve 50 is used to predict such a characteristic without actually measuring the contact resistance of the entire bond pad. Advantageously, measuring and/or plotting the hardness as a function of displacement depth of the nanoindenter tip 16 into the bond pad surface can be used as a good predictor to determine whether or not the contact resistance of the entire bond pad is suitable for subsequent multi-probe testing.

FIG. 6 shows actual test data correlating to plot 50 of FIG. 5 validating the consistent good electrical contact resistance for multiple die touchdowns into the bond pad under test.

Conversely, FIG. 7 depicts actual test data corresponding to plot 52 whereby the material hardness characteristics as a function of nanoindenter depth of the bond pad under test do not correlate with expected data, for instance, whereby the material hardness increases as a function of displacement depth into a die. In this particular sample, there is a noted peak 54 which has been found to be present in some bond pads that have contact resistance being unsuitable for multi-probe testing. While this peak 54 may not always be present, it is sometimes present which the present invention recognizes. Plot 52 is seen to deviate from the expected data plot 56, and for instance, by more than 20% from the predicted plot as represented by deviation D. For the data shown as 50 correlating to a sample having good contact resistance stability, this deviation D is within process parameters and the bond pad is advantageously predicted as having good contact resistance stability.

While the present invention in its most broadest embodiment recognizes the correlation of material hardness as a function of displacement depth to predict contact resistance stability, the present invention further provides that contact resistance can actually be measured locally, simultaneously, while measuring material hardness as a function of displacement depth to further ascertain the correlation of contact resistance at selected location under test to further accurately predict whether the entire bond pad sample has a stable contact resistance for multi-probe testing. For instance, the data obtained in FIGS. 6 and 7 can be utilized by processor 32 to correlate the contact resistance obtained proximate the indentation formed by tip 16 into the sample 14 to predict whether or not the overall contact resistance of the bond pad is within process specifications. For instance, the obtained contact resistance for multiple die touchdowns may be border line within process parameters such as shown at 58 in FIG. 7, but the curve of the material hardness as a function of penetration depth may/may not deviate enough from the predicted curve 56 to collectively lead to the determination that the bond pad contact resistance stability is or is not within process parameters specifications.

Turning now to FIG. 8, there is shown at 60 a methodology of the present invention for predicting bond pad contact resistance stability. At step 62, a bond pad is prepared upon the X-Y translator stage 12 of the nanoindenter 10.

At step 64, hardness and/or electrical properties of the bond pad are obtained at multiple points using apparatus 30. Hardness data as a function of penetration depth of the nanoindenter tip 16 is obtained, and plotted as shown in FIG. 5. The localized electrical contact resistance may also be obtained during this hardness testing by generating a current through the sample between the tip 16 and the sense probe 34, as shown in FIG. 3. The signal conditioner data acquisition system 32 obtains and processes all this obtained data at step 66. Specifically, the determined material hardness as a function of displacement depth of the tip 16 into sample 14 is analyzed by system 32 to determine whether or not the obtained data falls within process tolerance of the specification set for this process. In addition, if desired, the localized contact resistance for multiple die touchdowns is also obtained, such as shown in FIGS. 6 and 7, which data is analyzed to further correlate the contact resistance at the multiple points with the data obtained as shown in FIG. 5.

At step 70, the signal conditioner data acquisition system 32 ultimately determines whether or not the bond pad has a contact resistance stability suitable for multi-probe testing. Decision 70 may be made by only correlating the measured hardness as a function of displacement of the nanoindenter into the surface as shown in FIG. 5, or, in addition taking into account the localized contact resistance obtained by the nanoindenter to provide the determination whether or not the overall bond pad is predicted to be suitable for subsequent multi-probe testing.

The present invention achieves technical advantages by providing for the accurate prediction of whether or not contact resistance stability of a bond pad, rendered due to a change in process control or a current process control, leads to bond pads that are well suited for subsequent multi-probe testing. Advantageously, the nanoindentation technique is of lower cost than other techniques, is capable of sampling a large surface area, is less time intensive, and is significantly easier to interpret by a "non-expert" process technician. These features provide the many advantageous qualities that make this invention suitable for monitoring fab process changes that may impact contact resistance.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A method of testing a bond pad on a semiconductor device, comprising the steps of:

probing the bond pad with a first probe at a first location and measuring the mechanical properties of the bond pad as a function of probe depth and applied load to predict an electrical property of the bond pad.

2. The method as specified in claim 1 further comprising the step of using a nanoindenter type apparatus as the first probe to measure the bond pad semiconductor material mechanical properties as a function of the tip depth and applied load.

3. The method as specified in claim 1 further comprising the step of measuring an electrical property of the bond pad proximate the first location.

4. The method as specified in claim 3 further comprising the step of measuring the bond pad mechanical properties and a bond pad electrical property at multiple locations of the bond pad.

5. The method as specified in claim 3 further comprising the step of using a second probe to contact the bond pad proximate the first location to measure an electrical property.

6. The method as specified in claim 5 wherein a current is generated between the first probe and the second probe to measure an electrical property proximate the first location.

7. The method as specified in claim 3 further comprising the step of determining an electrical property of the bond pad by correlating the bond pad mechanical properties at the first location to the measured electrical property of the bond pad at the first location.

8. The method as specified in claim 1 further comprising the step of determining the presence of a thin film layer on the bond pad surface affecting an electrical property of the bond pad.

9. The method as specified in claim 1 further comprising the step of predicting the overall bond pad electrical property stability as a function of measuring the bond pad mechanical properties as a function of the indenter tip depth and applied load.

* * * * *